(12) United States Patent
Parker

(10) Patent No.: US 8,679,572 B2
(45) Date of Patent: Mar. 25, 2014

(54) COATED STENT

(75) Inventor: Fred T. Parker, Unionville, IN (US)

(73) Assignee: Cook Medical Technologies, LLC, Boomington, IN (US)

( * ) Notice: Subject to any disclaimer, the term of this patent is extended or adjusted under 35 U.S.C. 154(b) by 0 days.

(21) Appl. No.: 13/059,706

(22) PCT Filed: Aug. 25, 2009

(86) PCT No.: PCT/US2009/004832
§ 371 (c)(1),
(2), (4) Date: Mar. 14, 2011

(87) PCT Pub. No.: WO2010/024882
PCT Pub. Date: Mar. 4, 2010

(65) Prior Publication Data
US 2011/0268866 A1 Nov. 3, 2011

Related U.S. Application Data

(60) Provisional application No. 61/092,475, filed on Aug. 28, 2008.

(51) Int. Cl.
*B05D 3/00* (2006.01)
(52) U.S. Cl.
USPC .............. 427/2.3; 606/108; 606/194; 514/63; 427/2.25; 427/2.28; 427/2.24
(58) Field of Classification Search
USPC .............. 606/108; 623/1; 427/2.25, 2.3, 2.28; 514/63
See application file for complete search history.

(56) References Cited

U.S. PATENT DOCUMENTS

| 4,675,361 | A | | 6/1987 | Ward, Jr. | |
|---|---|---|---|---|---|
| 4,861,830 | A | | 8/1989 | Ward, Jr. | |
| 5,306,712 | A | * | 4/1994 | Tobitsuka et al. | 514/63 |
| 5,342,621 | A | | 8/1994 | Eury | |
| 5,843,089 | A | * | 12/1998 | Sahatjian et al. | 623/1.11 |
| 5,897,911 | A | * | 4/1999 | Loeffler | 427/2.25 |
| 5,911,752 | A | * | 6/1999 | Dustrude et al. | 623/1.1 |
| 6,375,787 | B1 | | 4/2002 | Lukic | |

(Continued)

OTHER PUBLICATIONS

Carrozza, Jr. et al., In Vivo Assessment of Stent Expansion and Recoil in Normal Porcine Coronary Arteries: Differential Outcome by Stent Design, 1999, Circulation, vol. 100, pp. 756-760.*

(Continued)

*Primary Examiner* — Dah-Wei Yuan
*Assistant Examiner* — Andrew Bowman
(74) *Attorney, Agent, or Firm* — Brinks Gilson & Lione

(57) ABSTRACT

A coated stent (20) for use in a medical procedure and methods of manufacturing the coated stent (20) are described. A stent component (30) has an expanded state in which an inner diameter ($d_s$) of the stent (30) is less than or equal to an outer diameter ($d_{c2}$) of a coating (40), thereby causing an inner surface (35) of the stent (30) to engage the outer surface (42) of the coating (40). In one exemplary method of manufacture, the stent (30) is disposed over the coating (40) when the coating (40) is provided with a first, smaller outer diameter ($d_{c1}$). The coating (40) then is radially expanded to a second, larger outer diameter ($d_{c2}$), which is greater than or equal to the inner diameter ($d_s$) of the stent (30), to cause the outer surface (42) of the coating (40) to engage the inner surface (35) of the stent (30).

20 Claims, 2 Drawing Sheets

(56) References Cited

U.S. PATENT DOCUMENTS

| | | |
|---|---|---|
| 6,752,826 B2 | 6/2004 | Holloway et al. |
| 6,939,377 B2 | 9/2005 | Jayaraman et al. |
| 7,108,716 B2 | 9/2006 | Burnside et al. |
| 7,288,111 B1 | 10/2007 | Holloway et al. |
| 7,297,159 B2 | 11/2007 | Hossainy et al. |
| 7,758,629 B2 | 7/2010 | Holloway et al. |
| 2002/0065552 A1 | 5/2002 | Jayaraman et al. |
| 2003/0120338 A1 | 6/2003 | Chobotov et al. |
| 2004/0062592 A1 | 4/2004 | Shekalim |
| 2004/0167606 A1 | 8/2004 | Chouinard |
| 2004/0213893 A1 | 10/2004 | Boulais |
| 2005/0113905 A1 | 5/2005 | Greenberg et al. |
| 2006/0136046 A1 | 6/2006 | Hartley et al. |
| 2006/0155364 A1 | 7/2006 | Holloway et al. |
| 2006/0196073 A1 | 9/2006 | Parker |
| 2006/0247761 A1 | 11/2006 | Greenberg et al. |
| 2007/0050010 A1 | 3/2007 | Bates et al. |
| 2007/0061002 A1 | 3/2007 | Paul, Jr. et al. |
| 2007/0088425 A1 | 4/2007 | Schaeffer |
| 2007/0179590 A1 | 8/2007 | Lu et al. |
| 2008/0015676 A1 | 1/2008 | Kantor |
| 2008/0190363 A1 | 8/2008 | Chen et al. |
| 2008/0213464 A1 | 9/2008 | O'Connor |

OTHER PUBLICATIONS

Pre-Brief Conference Request with Notice of Appeal for U.S. Appl. No. 12/337,863 dated Aug. 10, 2011, 7 pgs.

International Search Report and Written Opinion for PCT/US2009/004832 dated Oct. 26, 2009, 13 pgs.

Response to Written Opinion for PCT/US2009/004832, including Demand and amended claims, dated Jan. 13, 2010, 14 pgs.

International Preliminary Report on Patentability for PCT/US2009/004832 dated Nov. 2, 2010, 13 pgs.

Office Action for U.S. Appl. No. 12/337,863 dated Apr. 14, 2010, 9 pgs.

Response to Office Action for U.S. Appl. No. 12/337,863 filed Aug. 16, 2010, 9 pgs.

Final Office Action for U.S. Appl. No. 12/337,863 dated Nov. 2, 2010, 9 pgs.

Response to Final Office Action for U.S. Appl. No. 12/337,863 filed Jan. 31, 2011, 10 pgs.

Final Office Action for U.S. Appl. No. 12/337,863 dated Feb. 17, 2011, 8 pgs.

* cited by examiner

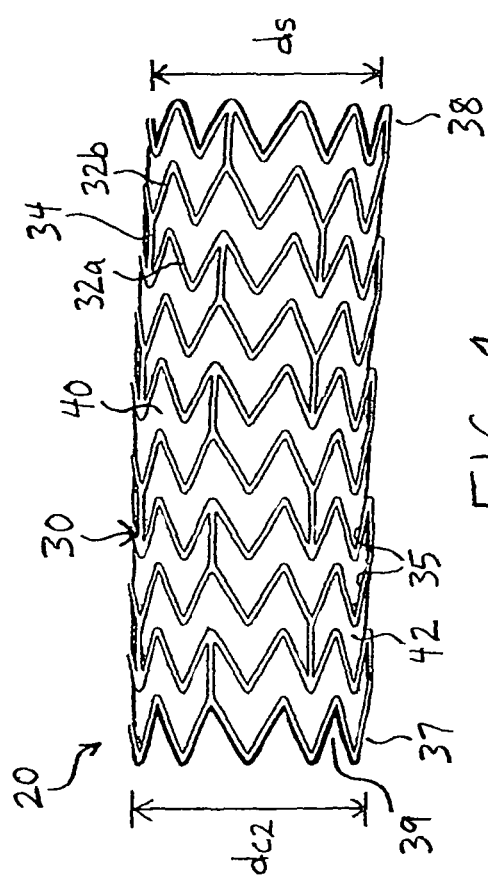
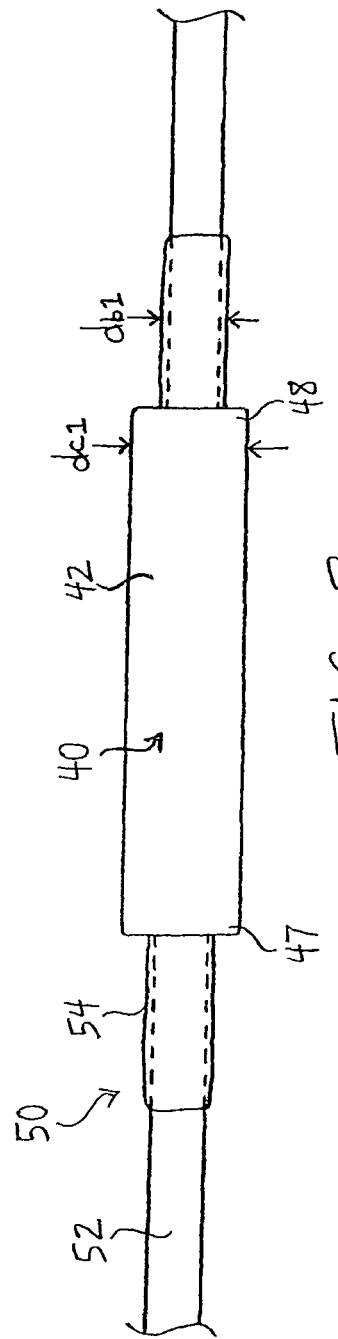
FIG. 1
FIG. 2

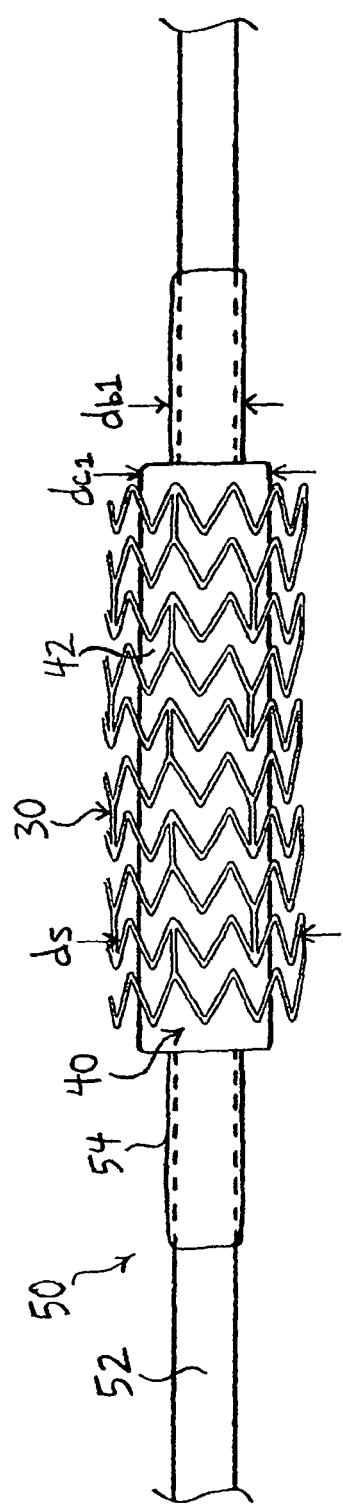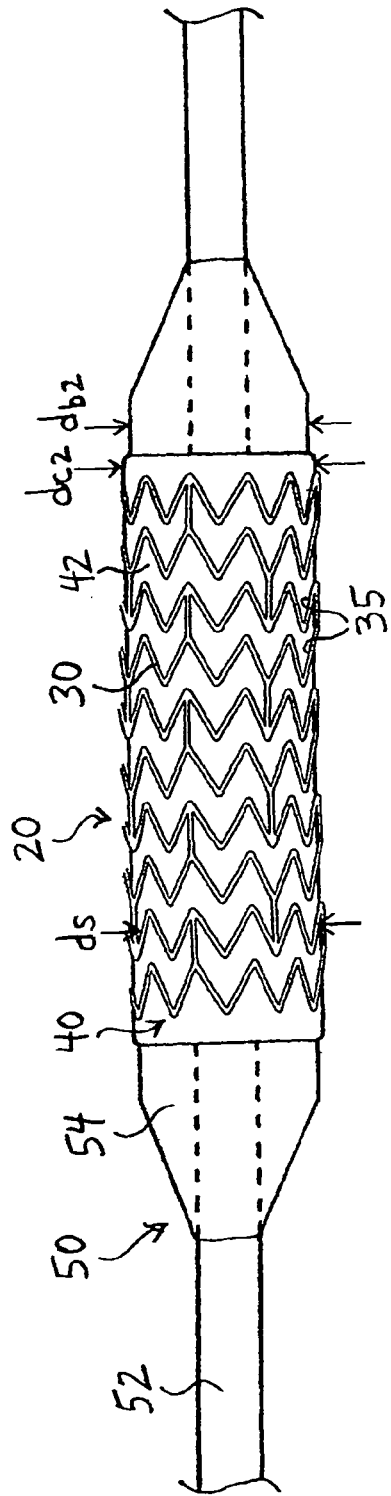

COATED STENT

RELATED APPLICATIONS

The present patent document is a §371 filing based on PCT Application Ser. No. PCT/US2009/004832, filed Aug. 25, 2009 (and published as WO 2010/024882A1 on Mar. 4, 2010), designating the United States and published in English, which claims the benefit of the filing date under 35 U.S.C. §119(e) of Provisional U.S. Patent Application Ser. No. 61/092,475, filed Aug. 28, 2008. All of the foregoing applications are hereby incorporated by reference in their entirety.

TECHNICAL FIELD

This invention relates to a method of coating a stent and to a coated stent. Embodiments of coated stents are envisaged for treating various medical conditions.

BACKGROUND ART

Stents may be inserted into an anatomical vessel or duct for various purposes. Stents are often used to maintain or restore patency in a formerly blocked or constricted passageway, for example, following a balloon angioplasty procedure. Some stents may be used in conjunction with a suitable coating to form a coated stent, for example, to treat an aneurysm or to deliver therapeutic agents disposed on the stent or coating in close proximity to a target site.

Stents may be either self-expanding or balloon-expandable, or they can have characteristics of both types of stents. Self-expanding stents may be delivered to a target site in a compressed configuration and subsequently expanded by removing a delivery sheath, removing trigger wires and/or releasing diameter-reducing ties. In a stent made of a shape-memory alloy such as nitinol, the shape-memory alloy may be employed to cause the stent to return to a predetermined configuration upon removal of the sheath or other device maintaining the stent in its predeployment configuration.

With balloon-expandable stents, the stent may be delivered and deployed using a catheter and one or more balloons disposed on the catheter. The stent may be coupled to the balloon during insertion until the target site is reached, and then deployed by inflating the balloon to expand the stent to bring the stent into engagement with the target site. Alternatively, the stent may be placed separately in the vessel and a subsequent catheter having an expansion portion may then be inserted into the stent to expand the stent at the target site.

When stents are used in conjunction with a coating, gaps may be formed between the stent and the coating. To reduce the formation of gaps, a coated stent typically comprises a first coating disposed internal to the stent and a second coating disposed external to the stent. Therefore, the stent is sandwiched between the first and second coatings to reduce or eliminate gap formation.

However, where first and second coatings are used, the profile of the stent is increased by at least one additional layer, which may make it difficult to use the stent in smaller vessels or ducts. Moreover, if first and second coatings are employed, it may increase the deployment forced needed to deploy the stent.

In view of the above, it would be desirable to provide a coated stent having few or no gaps formed between the stent and the coating, having a reduced profile, and which facilitates a reduction in deployment force.

DISCLOSURE OF THE INVENTION

According to a first aspect of the present invention, there is provided a method for coupling a stent to a coating, the method comprising: providing a coating comprising an outer surface having a first outer diameter in a first state; providing a stent having a compressed state and an expanded state, where an inner diameter of the stent in the expanded state is greater than the first outer diameter of the coating; aligning the stent with the coating when the coating is in the first state, such that at least a portion of the stent is disposed over the coating; and increasing the diameter of the coating to a second outer diameter, which is equal to or greater than the inner diameter of the stent, to at least partially embed an inner surface of the stent into the outer surface of the coating.

The method may further comprise exposing at least a portion of the coating to a solvent, prior to the step of increasing the diameter of the coating, to at least temporarily soften the coating.

The solvent may comprise dimethylacetamide.

In an embodiment, increasing the diameter of the coating comprises expanding the coating using a balloon catheter having an inflatable balloon.

The method may further comprise: softening at least a portion of the coating to facilitate expansion to the second outer diameter; increasing the diameter of the coating using the balloon to cause the outer surface of the coating to engage the inner surface of the stent; maintaining inflation of the balloon for a predetermined period of time to permit the coating to become secured to the stent; and deflating the balloon.

Preferably thermal techniques are used to at least partially melt the coating to facilitate at least one of expansion of the coating to the second outer diameter and embedding of the stent into the outer surface of the coating.

An outer surface of the stent may be substantially free of any coating.

According to a second aspect of the present invention there is provided a coated stent comprising: a coating comprising an outer surface having a first outer diameter in a first state; and a stent having a compressed state and an expanded state, where an inner diameter of the stent in the expanded state is greater than the first outer diameter of the coating so that the stent is configured to be at least partially disposed over the coating when the coating is in the first state, where the coating is adapted to be radially expanded to a second outer diameter equal to or greater than the inner diameter of the stent to at least partially embed an inner surface of the stent into the outer surface of the coating.

A solvent may be configured to be applied to at least a portion of the outer surface of the coating to facilitate expansion of the coating from the first outer diameter to the second outer diameter.

The solvent may comprise dimethylacetamide.

The coated stent may further comprise a balloon catheter having an inflatable balloon configured to increase the diameter of the coating from the first outer diameter to the second outer diameter.

An outer surface of the stent may be substantially free of any coating.

In a preferred embodiment the stent comprises a shape-memory material that is preconfigured to self-deploy to the expanded state, and expansion of the coating into engagement with the stent is configured to temporarily mechanically expand the diameter of the stent to a diameter beyond the preconfigured expanded state, where the strain imposed upon the stent is less than 10 percent during expansion of the coating.

According to a third aspect of the present invention, there is provided a method for coupling a stent to a coating, the method comprising: aligning at least a portion of a coating over a balloon of a balloon catheter; softening at least a portion of the coating to facilitate expansion of the coating from a first state having a first outer diameter to a second state having a second outer diameter; aligning a stent at least partially over the coating when the coating is in the first state; inflating the balloon to expand the coating from the first state to the second state, thereby causing an outer surface of the coating to engage an inner surface of the stent; maintaining inflation of the balloon for a predetermined period of time to permit the coating to become secured to the stent; and deflating the balloon.

Preferably an inner diameter of the stent in the expanded state is less than or equal to the second outer diameter of the coating to at least partially embed the inner surface of the stent into the outer surface of the coating.

The outer surface of the stent may be substantially free of any coating.

The step of softening at least a portion of the coating may comprise exposing at least a portion of the coating to a solvent.

Preferably the solvent comprises dimethylacetamide.

The method may further comprise using thermal techniques to at least partially melt the coating to facilitate at least one of expansion of the coating to the second outer diameter and embedding of the stent into the outer surface of the coating.

In an embodiment the stent comprises a shape-memory material that is preconfigured to self-deploy to the expanded state, and the method further comprises expanding the coating into engagement with the stent and temporarily mechanically expanding the diameter of the stent to a diameter beyond the preconfigured expanded state.

Embodiments of the present invention provide a coated stent for use in a medical procedure and methods of manufacturing a coated stent. The stent component has an expanded state having an inner diameter that is less than or equal to an outer diameter of the coating, thereby causing an inner surface of the stent to engage, and at least partially embed into, an outer surface of the coating. The outer surface of the stent may remain substantially or completely free of any coating.

In one example, the coating may comprise a biocompatible polymeric material. For example, the coating may comprise Thoralon®. The stent may comprise a shape-memory material, such as a nickel-titanium alloy.

In one exemplary method of manufacture, the stent is disposed over the coating when the coating is in a first state having a first outer diameter. The coating then is adapted to be radially expanded to a second outer diameter, which is greater than or equal to the inner diameter of the stent. This causes the outer surface of the coating to engage, and preferably at least partially embed into, the inner surface of the stent.

At least a portion of the outer surface of the coating may be softened to facilitate expansion of the coating from the first outer diameter to the second outer diameter. For example, a solvent such as dimethylacetamide may at least temporarily soften the outer surface of the coating. A balloon catheter having an inflatable balloon then may be used to expand the softened coating from the first outer diameter to the second outer diameter, thereby causing the outer surface of the coating to engage the inner surface of the stent. The balloon may be inflated for a predetermined period of time to permit the coating to at least partially dry, set, or otherwise become secured to the stent.

Advantageously, since the outer diameter of the coating in the second state is equal to or greater than the inner diameter of the stent, the inner surface of the stent may engage, and at least partially embed into, the outer surface of the coating. If the coating comprises Thoralon®, which may be soft and relatively sticky, then the inner surface of the stent may embed into and securely engage the coating to reduce or eliminate gap formation between the stent and the coating. Moreover, since the stent may be securely disposed over or in the coating with little or no gap formation, application of a second coating over the stent may not be necessary.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

Preferred embodiments are now described, by way of example only, with reference to the accompanying drawings, in which:

FIG. 1 is a side view of a coated stent;

FIG. 2 is a side view of a coating disposed over a balloon;

FIG. 3 is a side view of a stent being disposed over the coating and the balloon of FIG. 2; and FIG. 4 is a side view depicting the engagement of the coating with the stent of FIG. 3.

The components in the Figures are not necessarily to scale, emphasis instead being placed upon illustrating the principles of the invention. Moreover, in the Figures, like reference numerals designate corresponding parts throughout the different views.

DESCRIPTION OF THE PREFERRED EMBODIMENTS

In the present application, the term "proximal" refers to a direction that is generally closest to the heart during a medical procedure, while the term "distal" refers to a direction that is furthest from the heart during a medical procedure.

Referring now to FIG. 1, a coated stent 20 is shown after manufacture, preferably according to one or more of the techniques described hereinbelow. The coated stent 20 comprises at least one stent 30 and a coating 40. As used in the present application, the terms "coated" and "coating" generally refer to the provision of one or more layers of material that are separate from the stent itself. The "coating" need not be disposed external to the stent 30, and in the examples described herein, the coating 40 is generally disposed internal to the stent 30, or the stent 30 may be at least partially embedded in the coating 40, as depicted in FIG. 1 and explained further below.

The coated stent 20 may be used in a wide range of procedures, for example, to treat an aneurysm, stenosis or other condition. The stent 30 generally provides the radial force needed to expand the coated stent 20 into engagement at a target site, while the coating 40 may provide a barrier having a selected porosity and may be suitable for delivering one or more therapeutic agents, as explained further below. A lumen 39 may be formed internal to the coating 40 and may be suitable for carrying fluid though the coated stent 20.

The stent 30 may be made from numerous metals and alloys. In one example described further below, the stent 30 comprises a shape-memory material such as a nickel-titanium alloy ("nitinol"). Moreover, the structure of the stent 30 may be formed in a variety of ways to provide a suitable intraluminal support structure. For example, one or more stents 30 may be made from a woven wire structure, a laser-cut cannula, individual interconnected rings, or another pattern or design.

In one example, the stent 30 may be configured in the form of one or more "Z-stents" or Gianturco stents, each of which may comprise a series of substantially straight segments interconnected by a series of bent segments. The bent segments may comprise acute bends or apices. The Gianturco stents are arranged in a zigzag configuration in which the straight segments are set at angles relative to each other and are connected by the bent segments.

In the examples shown herein, the structure of the stent 30 is similar to the commercially available ZILVER® stent, manufactured by Cook Incorporated of Bloomington, Ind. As shown in FIG. 1, the stent 30 may be formed from a slotted tube generally comprising a series of adjacent segments 32a and 32b and a pattern of connecting segments 34 disposed therebetween. One or more eyelets (not shown) may extend from the proximal end 37 and the distal end 38 of the stent 30, and the eyelets may include a radiopaque material such as gold to provide radiographic visualisation of the stent's position when placed in the vessel or duct of a patient. However, as noted above and explained further below, the stent 30 may comprise any suitable configuration and one or more stents may be provided.

The coating 40 may comprise a polymeric sheet having any suitable porosity. The porosity may be substantially porous or substantially non-porous and may be selected depending on the application. In one example, a porous polymeric sheet may comprise the polyurethane Thoralon®, as described in U.S. Pat. No. 6,939,377, incorporated herein by reference in its entirety, Thoralon® is a polyetherurethane urea blended with a siloxane-containing surface modifying additive. Specifically, the polymer is a mixture of base polymer BPS-215 and an additive SMA-300. The concentration of additive may be in the range of 0.5% to 5% by weight of the base polymer. The BPS-215 component (Thoratec® Corporation, Pleasanton, Calif.) is a segmented polyether urethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED). The SMA-300 component (Thoratec® Corporation, Pleasanton, Calif.) is a polyurethane comprising polydimethylsiloxane as a soft segment and the reaction product of MDI and 1,4-butanediol as a hard segment. A process for synthesizing SMA-300 is described, for example, in U.S. Pat. Nos. 4,861,830 and 4,675,361, which are incorporated herein by reference in their entirety. A porous polymeric sheet can be formed from these two components by dissolving the base polymer and additive in a solvent such as dimethylacetamide and solidifying the mixture by solvent casting or by coagulation in a liquid that is a non-solvent for the base polymer and additive.

Thoralon® has been used in certain vascular applications and is characterised by thromboresistance, high tensile strength, low water absorption, low critical surface tension, and good flex life. Thoralon® is believed to be biostable and to be useful in vivo in long term blood contacting applications requiring biostability and leak resistance. Because of its flexibility, Thoralon® may be useful in larger vessels, such as the abdominal aorta, where elasticity and compliance are beneficial.

Further, Thoralon® may also be used as a drug delivery vehicle, for example, to deliver one or more therapeutic agents. The therapeutic agents may be coated onto or contained within a porous outer layer of the coating 40 for sustained release subsequent to an implantation procedure and may be used, for example, to promote intimal cell in-growth.

While Thoralon® is generally described herein, the coating 40 may comprise other materials. In addition to, or in lieu of, a porous polyurethane such as Thoralon®, the coating 40 may comprise any biocompatible polymeric material including non-porous polyurethanes, PTFE, expanded PTFE (ePTFE), polyethylene tetraphthalate (PET), aliphatic polyoxaesters, polylactides, polycaprolactones, and hydrogels. The coating 40 also may comprise a graft material, such as Dacron®, which may optionally be heat treated and/or partially melted.

The stent 30 has a compressed, reduced diameter delivery state in which the coated stent 20 may be advanced to a target location within a vessel, duct or other anatomical site. The stent 30 further has an expanded state, as shown in FIG. 1, in which it may be configured to apply a radially outward force upon the vessel, duct or other target location, e.g., to maintain patency within a passageway. In the expanded state, fluid flow is allowed through the lumen 39 of the coated stent 20.

The stent 30 may comprise predetermined inner and outer diameters in the expanded state. The outer diameter of the stent in the expanded state may be sized for a particular purpose, e.g., to engage an inner wall of a vessel or duct. As shown in FIG. 1, and explained further below, an inner diameter $d_s$ of the stent 30 may be sized for snug engagement with an outer surface 42 of the coating 40. In one example, the coating 40 may be expanded to a second outer diameter $d_{c2}$, which is greater than or equal to the inner diameter $d_s$ of the stent 30, and securely coupled to the stent 30, as explained in greater detail below.

If the stent 30 comprises a shape-memory material such as nitinol, the stent may be manufactured such that it can assume the preconfigured expanded inner and outer diameters upon application of a certain cold or hot medium. More specifically, a shape-memory material may undergo a substantially reversible phase transformation that allows it to "remember" and return to a previous shape or configuration. For example, in the case of nitinol, a transformation between an austenitic phase and a martensitic phase may occur by cooling and/or heating (shape memory effect) or by isothermally applying and/or removing stress (superelastic effect). Austenite is characteristically the stronger phase and martensite is the more easily deformable phase.

In an example of the shape-memory effect, a nickel-titanium alloy having an initial configuration in the austenitic phase may be cooled below a transformation temperature $(M_f)$ to the martensitic phase and then deformed to a second configuration. Upon heating to another transformation temperature $(A_f)$, the material may spontaneously return to its initial, predetermined configuration. Generally, the memory effect is one-way, which means that the spontaneous change from one configuration to another occurs only upon heating. However, it is possible to obtain a two-way shape memory effect, in which a shape memory material spontaneously changes shape upon cooling as well as upon heating.

Referring now to FIGS. 2 to 4, one or more techniques suitable for manufacturing the coated stent 20 of FIG. 1 are described. In a first step, a film sleeve of the coating 40 may be provided, as shown in FIG. 2. As noted above, the coating 40 may comprise any number of suitable materials. The generally tubular film sleeve may be formed around a mandrel, for example, as explained in U.S. patent application Ser. No. 12/337,863 (published as US 2009/017454), which is hereby incorporated by reference in its entirety. In one embodiment, an inert mandrel, such as a glass mandrel, may be immersed or sprayed with a composition to form the coating 40 having a desired configuration. In one example, the mandrel may be cleaned with isopropyl alcohol. The composition of the coating 40 may be prepared by dissolving a polymer in a solvent including alcohols, aromatic hydrocarbons, dimethylacetamide, and the like. The composition may be varied to obtain the desired viscosity of the coating 40. If Thoralon® is the selected polymer, as noted above, and dimethylacetamide is the selected solvent, the polymer may comprise about 5% to about 40% by weight of the total weight of the composition.

In one example, the mandrel may be immersed in the composition at a predetermined speed through a die, and the solvent then can be removed or allowed to evaporate to form a film layer of the coating 40 on the mandrel. Further, evaporation of the solvent can be induced by application of heat treatment for about 5 minutes to about 24 hours in an oven having a temperature of about 25 to about 80 degrees Celsius. Alternatively, vacuum conditions may be employed. The finished coating 40 comprises a first outer diameter $d_{c1}$ and has a first end 47 and a second end 48 as shown in FIG. 2.

As will be explained further below, the coating 40 may be expanded to the second outer diameter $d_{c2}$, shown in FIG. 1, using a balloon catheter 50. The balloon catheter 50 may comprise a flexible, tubular member 52 having a balloon 54 coupled thereto. The tubular member 52 may be formed from one or more semi-rigid polymers and the balloon 54 may be manufactured from any suitable balloon material used during an interventional procedure, such as PEBAX, nylon, Hytrel, Arnitel, or other polymers. The balloon 54 has an uninflated state and an inflated state having outer diameters $d_{b1}$ and $d_{b2}$, respectively. The coating 40 may be placed over the balloon 54 and aligned with the balloon when the balloon is in the uninflated state having the diameter $d_{b1}$, as shown in FIG. 2. Optionally, the balloon 54 may be partially expanded at this time to lightly engage an inner surface of the coating 40, thereby providing a frictional engagement suitable for preventing the coating 40 from moving with respect to the balloon 54. Other techniques may be employed to secure the position of the coating 40 with respect to the balloon 54.

At least a portion of the coating 40 may be softened, for example, by applying a substance such as a solvent, to facilitate subsequent expansion of the coating 40 by the balloon catheter 50. By way of example, if a Thoralon® coating is employed, a solvent such as dimethylacetamide may be used to soften a portion of the coating 40. However, other solvents, such as alcohols, aromatic hydrocarbons, and the like may be used to soften at least a portion of the coating 40.

In one embodiment, at least a portion of the outer surface 42 of the coating 40 may be exposed to the solvent, for example, by immersing, spraying, brushing, or otherwise applying the solvent to the coating 40. Depending on the length of time that the coating 40 is exposed to the solvent, selected regions of the coating 40 may become at least temporarily softened and/or tacky. Preferably, at least a portion of the outer surface 42 of the coating 40 becomes softened and/or tacky, regardless of the effect of the solvent on the remainder of the coating 40.

Referring now to FIG. 3, in another step, the stent 30 may be placed over the balloon catheter 50 and the coating 40. Preferably, the stent 30 is advanced over the coating 40 when the stent 30 is in a fully expanded state and the balloon 54 is partially or entirely deflated. Notably, the inner diameter $d_s$ of the stent 30 in the expanded state is greater than the first outer diameter $d_{c1}$ of the coating 40.

Referring now to FIG. 4, with the stent 30 aligned over the coating 40, and the coating 40 comprising a softened and/or tacky outer surface 42, the balloon 54 may be inflated. Specifically, an inflation fluid may be provided through a lumen of the tubular member 52 and into the inner confines of the balloon 54 to expand the balloon to the inflated state having the diameter $d_{b2}$, as shown in FIG. 4. The coating 40 therefore may be expanded to a second state having the second outer diameter $d_{c2}$, as shown in FIG. 4. The second outer diameter $d_{c2}$ of the coating 40 preferably is equal to or greater than the inner diameter $d_s$ of the stent 30, thereby causing the coating 40 securely to engage the inner surface 35 of the stent 40. Preferably, since an outer surface 42 of the coating 40 is softened and/or tacky as explained above, the stent 30 may become at least partially embedded into the outer surface 42 of the coating 40.

The balloon 54 may remain in the inflated state having the outer diameter $d_{b2}$ for a predetermined period of time, such as a time sufficient to permit the outer surface 42 of the coating 40 partially or completely to dry, set, or otherwise become secured to the stent 30. After the predetermined time, the balloon 54 may be deflated, leaving the coating 40 securely coupled to the stent 30. The first and second ends 47, 48 of the coating 40 then may be trimmed or modified to comport to the shapes of the corresponding ends 37 and 38 of the stent 30, as depicted in FIG. 1.

It should be noted that during expansion of the balloon 54, while the coating 40 is expanded into engagement with the stent 30, the balloon 54 may mechanically expand the diameter of the stent 30 to a larger inner diameter that is beyond its heat-set inner diameter $d_s$. As long as the strain imposed upon the stent 30 is less than about 10%, and more preferably less than about 6%, it is expected that the stent 30 will not be permanently deformed, but rather may return to its preconfigured heat-set shape.

Advantageously, since the stent 30 has a preconfigured inner diameter $d_s$ that is less than or equal to the second outer diameter $d_{c2}$ of the coating 40, gaps between the stent 30 and the coating 40 may be reduced or eliminated. If the coating 40 comprises a substance having a relatively soft and sticky nature (such as Thoralon®), the inner surfaces 35 of the stent 40 may become at least partially embedded into the outer surface 42 of the coating 40. Therefore, the need for a separate adhesive to couple the stent 30 to the coating 40 may be avoided.

Moreover, since potential gaps between the stent 30 and the coating 40 are substantially reduced or eliminated, there may be no need to place an additional coating over the stent 30. By reducing the number of coatings or layers coupled to the stent 30, the stent 30 may comprise a less bulky profile and the force necessary to deploy the stent 30 may be reduced.

In another embodiment, the outer surface 42 of the coating 40 may be melted using thermal techniques to facilitate expansion of the coating 40 by the balloon 54, and/or to facilitate embedding of the coating 40 with the stent 30. For example, prior to expansion of the coating 40, the outer surface 42 of the coating 40 may be at least partially melted using thermal techniques including but not limited to convection, radiant, radiofrequency or other heating techniques. By at least partially melting the coating 40, the coating 40 may be softened to facilitate expansion from the first outer diameter $d_{c1}$ to the second outer diameter $d_{c2}$. Additionally, heat may be applied to the stent 30 and the coating 40 when the balloon 54 is inflated to at least partially melt to the outer surface 42 and facilitate embedding of the coating 40 with the stent 30.

Such thermal techniques may be used in conjunction with the use of a solvent, as described above, or may be used alone to effect expansion of the coating 40 and attachment of the coating 40 to the stent 30, i.e., in lieu of a solvent. It should be noted that if the stent 30 comprises a shape-memory alloy such as nitinol, then the temperature used to heat and partially melt the coating 40 preferably does not exceed a threshold, such as 700 degrees Fahrenheit (370 degrees Celcius), which may otherwise affect the shape-memory properties of nitinol.

The coated stent 20 may be delivered into a vessel, duct, or other anatomical site using a suitable deployment system or introducer. An introducer, such as that described in PCT publication WO 98/53761, entitled "A Prosthesis and a Method and Means of Deploying a Prosthesis," which is incorporated herein by reference in its entirety, may be used to deploy the stent-grafts. WO 98/53761 describes a deployment system for an endoluminal prosthesis whereby the prosthesis is radially compressed onto a delivery catheter and is covered by an outer sheath. To deploy the system, the operator slides or retracts the outer sheath over the delivery catheter, thereby exposing the prosthesis. The prosthesis expands outwardly upon removal of the sheath. The operator can directly manipulate the sheath and the delivery catheter, which provides the operator with a relatively high degree of control during the procedure. Further, such delivery devices may be compact and may have a relatively uniform, low-diameter radial profile, allowing for atraumatic access and delivery.

As noted above, in other examples, the stent 30 may comprise other shapes. Further, multiple stents 30 may be provided and individually coupled to the coating 40. For example, several individual Z-stents may be secured to the coating 40 in the manner described above. Similarly, one or more stents may be circumferentially wound in a continuous fashion to form a coil or helical wire structure, and then attached to the coating 40 using the techniques described herein. In each instance, since an inner diameter of the stent 30 is less than or equal to the second outer diameter of the coating 40, gaps between the stent and coating may be reduced and the need for an additional coating may be eliminated.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

The disclosures in U.S. 61/092,475, from which the present application claims priority, and in the abstract accompanying this application are incorporated herein by reference.

The invention claimed is:

1. A method for coupling a stent to a polymeric coating for delivery of one or more therapeutic agents, the method including:
    aligning at least a portion of a polymeric coating over a balloon of a balloon catheter;
    softening at least a portion of the polymeric coating to facilitate expansion of the polymeric coating from a first state having a first outer diameter to a second state having a second outer diameter;
    aligning a stent at least partially over the polymeric coating when the polymeric coating is in the first state;
    inflating the balloon to expand the polymeric coating from the first state to the second state, wherein the balloon is expanded to a diameter greater than or equal to a predetermined deployed diameter of the stent to at least partially embed the inner surface of the stent into the outer surface of the polymeric coating;
    maintaining inflation of the balloon for a predetermined period of time to permit the polymeric coating to become secured to the inner surface of the stent to create a coated stent;
    deflating the balloon; and
    thereafter compressing the stent onto a delivery catheter.

2. A method as claimed in claim 1, wherein no separate step of coating the outer surface of the stent is carried out.

3. A method as claimed in claim 1, wherein the step of softening at least a portion of the polymeric coating includes exposing at least a portion of the polymeric coating to a solvent.

4. A method as claimed in claim 3, wherein the solvent includes dimethylacetamide.

5. A method as claimed in claim 1 further comprising using a thermal technique at least partially to melt the polymeric coating to facilitate expansion of the polymeric coating to the second outer diameter and/or embedding of the stent into the outer surface of the polymeric coating.

6. A method as claimed in claim 1, wherein the stent includes a shape-memory material that is preconfigured to self-deploy to the expanded state, the method including expanding the polymeric coating into engagement with the stent and temporarily mechanically expanding the diameter of the stent beyond the preconfigured expanded state.

7. The method of claim 1 wherein at least one of first and second ends of the coating is modified to comport to a shape of one of first and second ends of the stent after the balloon is deflated.

8. The method of claim 1 wherein the step of softening at least a portion of the polymeric coating occurs prior to delivery of the stent to a target site within the body.

9. The method of claim 1 wherein initial inflation of the balloon occurs when the stent is already in an expanded state.

10. The method of claim 1 wherein the predetermined period of time that the balloon is inflated occurs outside of the body.

11. A method for coupling a stent to a polymeric coating for delivery of one or more therapeutic agents, the method including:
    aligning at least a portion of a polymeric coating over a balloon of a balloon catheter;
    softening at least a portion of the polymeric coating to facilitate expansion of the polymeric coating from a first state having a first outer diameter to a second state having a second outer diameter;
    aligning a stent at least partially over the polymeric coating when the polymeric coating is in the first state;
    inflating the balloon to expand the polymeric coating from the first state to the second state, thereby causing the outer surface of the polymeric coating to engage the inner surface of the stent;
    maintaining inflation of the balloon for a predetermined period of time to permit the polymeric coating to become secured to the inner surface of the stent to create a coated stent;
    deflating the balloon,
    wherein at least one of first and second ends of the coating is modified to comport to a shape of one of first and second ends of the stent after the balloon is deflated;
    thereafter compressing the stent onto a delivery catheter.

12. The method of claim 11, wherein an inner diameter of the stent in its expanded state is less than or equal to the second outer diameter of the polymeric coating.

13. The method of claim 12, wherein no separate step of coating the outer surface of the stent is carried out.

14. The method of claim 11, wherein the step of softening at least a portion of the polymeric coating includes exposing at least a portion of the polymeric coating to a solvent.

15. The method of claim 14, wherein the solvent includes dimethylacetamide.

16. The method of claim 11 further comprising using a thermal technique at least partially to melt the polymeric coating to facilitate expansion of the polymeric coating to the second outer diameter and/or embedding of the stent into the outer surface of the polymeric coating.

17. The method of claim 11, wherein the stent includes a shape-memory material that is preconfigured to self-deploy to the expanded state, the method including expanding the polymeric coating into engagement with the stent and temporarily mechanically expanding the diameter of the stent beyond the preconfigured expanded state.

18. The method of claim 11 wherein the step of softening at least a portion of the polymeric coating occurs prior to delivery of the stent to a target site within the body.

19. The method of claim 11 wherein initial inflation of the balloon occurs when the stent is already in an expanded state.

20. The method of claim 11 wherein the predetermined period of time that the balloon is inflated occurs outside of the body.

* * * * *